United States Patent
Talamine et al.

(10) Patent No.: US 8,648,255 B2
(45) Date of Patent: Feb. 11, 2014

(54) LASER BEAM BUTTON WELD OF DISSIMILAR MATERIALS

(75) Inventors: Ken Talamine, Amherst, NY (US); Donald Anthony Bonitati, Orchard Park, NY (US); Joseph M. Prinzbach, North Tonawanda, NY (US); Keith Seitz, Clarence Center, NY (US)

(73) Assignee: Greatbatch Ltd., Clarence, NY (US)

( * ) Notice: Subject to any disclaimer, the term of this patent is extended or adjusted under 35 U.S.C. 154(b) by 209 days.

(21) Appl. No.: 13/112,041

(22) Filed: May 20, 2011

(65) Prior Publication Data

US 2011/0284284 A1 Nov. 24, 2011

Related U.S. Application Data

(60) Provisional application No. 61/346,921, filed on May 21, 2010.

(51) Int. Cl.
*H01J 5/00* (2006.01)

(52) U.S. Cl.
USPC ............. 174/50.6; 174/650; 607/37; 361/302

(58) Field of Classification Search
USPC ........... 174/650, 50.6, 35 R; 361/302; 607/37
See application file for complete search history.

(56) References Cited

U.S. PATENT DOCUMENTS

| | | | |
|---|---|---|---|
| 4,252,263 A | 2/1981 | Houston | |
| 5,250,373 A | 10/1993 | Muffoletto et al. | |
| 5,571,146 A | 11/1996 | Jones et al. | |
| 5,750,286 A | 5/1998 | Paulot et al. | |
| 6,061,595 A | 5/2000 | Safarevich | |
| 6,503,640 B2 | 1/2003 | Wittebrood et al. | |
| 6,852,925 B2 * | 2/2005 | Wolf et al. | 174/50.6 |
| 6,929,881 B2 | 8/2005 | Wutz et al. | |
| 6,932,879 B2 | 8/2005 | Ely et al. | |
| 7,145,076 B2 * | 12/2006 | Knappen et al. | 174/50.6 |
| 7,341,802 B1 | 3/2008 | Ota et al. | |
| 7,539,007 B2 | 5/2009 | Zhao et al. | |
| 7,544,220 B2 | 6/2009 | Zhao et al. | |
| 7,564,674 B2 * | 7/2009 | Frysz et al. | 361/302 |
| 7,622,219 B2 | 11/2009 | Ota et al. | |
| 7,660,093 B2 * | 2/2010 | Krause | 361/117 |
| 2004/0038070 A1 | 2/2004 | Dockus et al. | |
| 2005/0007718 A1 | 1/2005 | Stevenson | |
| 2006/0259093 A1 | 11/2006 | Stevenson | |
| 2008/0171952 A1 | 7/2008 | Mishima | |

OTHER PUBLICATIONS

European Search Report dated Oct. 4, 2011.

* cited by examiner

*Primary Examiner* — Dhirubhai R Patel
(74) *Attorney, Agent, or Firm* — Michael F. Scalise

(57) ABSTRACT

Terminal pins that include a refractory metal partially welded to a terminal block of a dissimilar metal incorporated into feedthrough filter capacitor assemblies are discussed. The feedthrough filter capacitor assemblies are particularly useful for incorporation into implantable medical devices such as cardiac pacemakers, cardioverter defibrillators, and the like, to decouple and shield internal electronic components of the medical device from undesirable electromagnetic interference (EMI) signals.

26 Claims, 3 Drawing Sheets

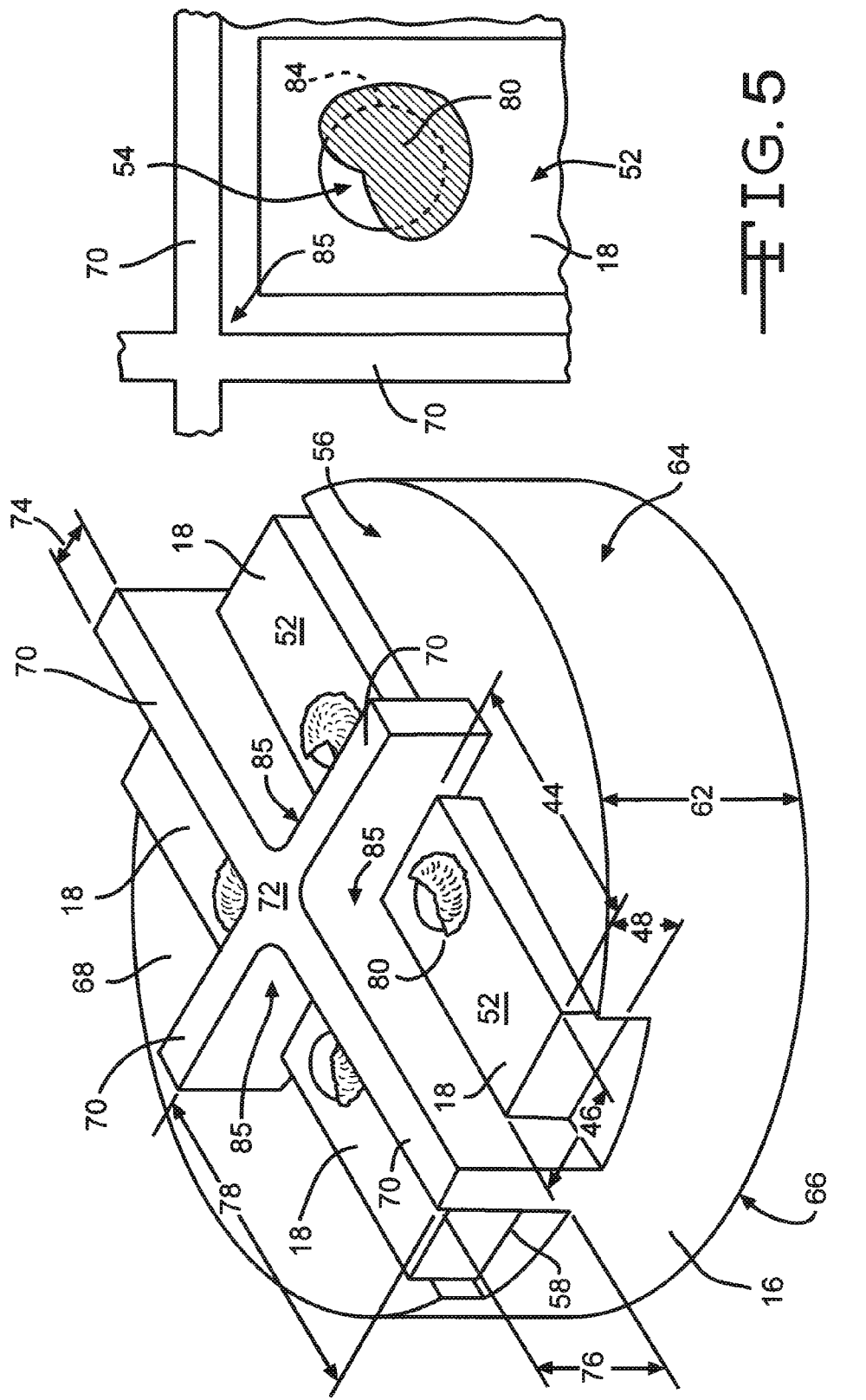

LASER BEAM BUTTON WELD OF DISSIMILAR MATERIALS

CROSS-REFERENCE TO RELATED APPLICATIONS

This application claims priority from U.S. Provisional Patent Application Ser. No. 61/346,921, filed May 21, 2010.

1. FIELD OF THE INVENTION

This invention relates generally to a hermetic feedthrough terminal pin assembly, preferably of the type incorporating a filter capacitor. More specifically, this invention relates to a method of welding two dissimilar metals into feedthrough filter capacitor assemblies, particularly of the type used in implantable medical devices such as cardiac pacemakers, cardioverter defibrillators, and the like, to decouple and shield internal electronic components of the medical device from undesirable electromagnetic interference (EMI) signals.

2. PRIOR ART

Feedthrough assemblies are generally well known in the art for use in connecting electrical signals through the housing or case of an electronic instrument. For example, in an implantable medical device, such as a cardiac pacemaker, defibrillator, or neurostimulator, the feedthrough assembly comprises one or more conductive terminal pins supported by an insulator structure for passage of electrical signals from the exterior to the interior of the medical device. The conductive terminals are fixed into place using a gold brazing process, which provides a hermetic seal between the pin and insulative material.

Since feedthrough assemblies such as these are implanted in human bodies, it is generally preferred that the materials used to construct such assemblies are biocompatible. These biocompatible materials, although commonly considered to be immune to the human body, generally have different material properties. These differing material properties such as melting temperature, thermal expansion, thermal conductivity and electrical conductivity make these materials difficult to join and construct into a feedthrough assembly.

Feedthrough assemblies generally comprise an insulative body, a supporting ferrule, and a plurality of electrically conductive feedthrough terminal pins that are hermetically sealed in the insulative body. In some cases, a capacitor is also incorporated into the assembly to provide protection from electromagnetic interface (EMI). With respect to the present invention, additional metallic terminal blocks, incorporated with a polymeric body, are integrated in the feedthrough assembly. Nevertheless, the electrically conductive feedthrough terminal pins are preferrably electrically connected to these metallic terminal blocks located adjacent the polymeric body.

Terminal pins have been composed of niobium and niobium alloys. Niobium and niobium alloys are biocompatible refractory metals that are cost effective. The niobium material provides good mechanical strength and electrical conduction, which adds to the durability and performance of the feedthrough. However the refractive nature of the niobium metal makes it a difficult material with which to join to other metals, particularly non-refractive metals such as nickel.

In addition to the difficulties in joining dissimilar metals, other constraints from adjacent materials of the feedthrough assembly present additional difficulties which need to be overcome in constructing feedthrough assemblies. For example, the generally lower melting temperatures of adjacent polymeric bodies provide additional constraining parameters, particularly when they are located adjacent to where dissimilar metals are being joined together. The present invention addresses these problems as it relates to the construction of feedthrough assemblies. The present invention further provides an optimal construction and joining process thereof by which dissimilar metals are joined in the construction of feedthrough assemblies.

SUMMARY OF THE INVENTION

In a preferred form, a feedthrough filter capacitor assembly according to the present invention comprises an outer ferrule hermetically sealed to either an alumina insulator or fused glass dielectric material seated within the ferrule. The insulative material is also hermetically sealed to at least one terminal pin. That way, the feedthrough assembly prevents leakage of fluid, such as body fluid in a human implant application, past the hermetic seal at the insulator/ferrule and insulator/terminal pin interfaces.

According to the invention, the terminal pin of a feedthrough assembly, and preferably of the feedthrough filter capacitor assembly, is composed of a biocompatible refractive metal, such as niobium. The terminal pin can be a uniform wire-type structure of niobium or an alloy thereof. In that respect, niobium is a corrosion resistant material that provides a more cost effective terminal pin than other conventional metals, such as platinum or platinum-iridium terminal pins. Furthermore, terminal pins composed of niobium achieve the same benefits of biocompatibility, good mechanical strength, electrical conduction and a reliable hermetic feedthrough seal.

A plurality of terminal blocks are each preferably positioned in a slot atop a polymeric protective cap which preferably resides within the proximal region of the feedthrough assembly. The plurality of terminal blocks, preferably composed of an electrically conductive metal such as nickel, provides a preferred means of electrically attaching the feedthrough assembly to a medical device.

These terminal blocks provide a larger surface area with which to attach electrical connections between the feedthrough assembly and the medical device. The protective cap, composed of a biocompatible polymeric material, electrically insulates each individual terminal block and protects the feedthrough assembly from possible mechanical damage.

The specific design parameters and material properties comprising the feedthrough assembly, of the present invention, present particular constraints regarding the connection of the terminal pin to the terminal block. As such, the present invention provides a feedthrough assembly and manufacturing process thereof that effectively joins these two dissimilar metals of the terminal pin and block. Particularly, the joining of the terminal block to the terminal pin, without causing damage to the adjacent polymeric protective cap is discussed.

These and other objects and advantages of the present invention will become increasingly more apparent by a reading of the following description in conjunction with the appended drawings.

BRIEF DESCRIPTION OF THE DRAWINGS

FIG. 4 is a magnified perspective of the view of the perspective an alternate perspective view of the cutter housing of the present invention.

FIG. 5 is a magnified top view showing an embodiment of one of the welds of the present invention.

DETAILED DESCRIPTION OF THE PREFERRED EMBODIMENTS

Figure 1:
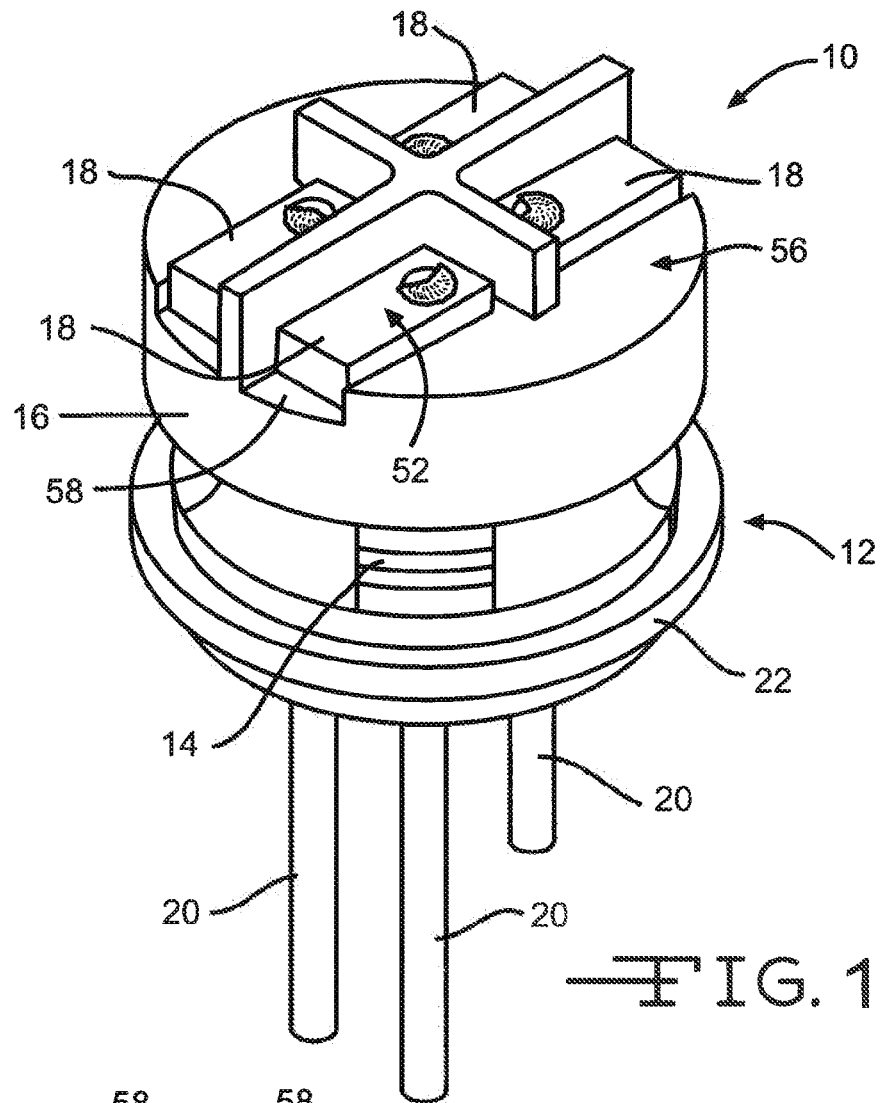
FIG. 1 is a perspective view of a feedthrough filter capacitor assembly.
Figure 3:
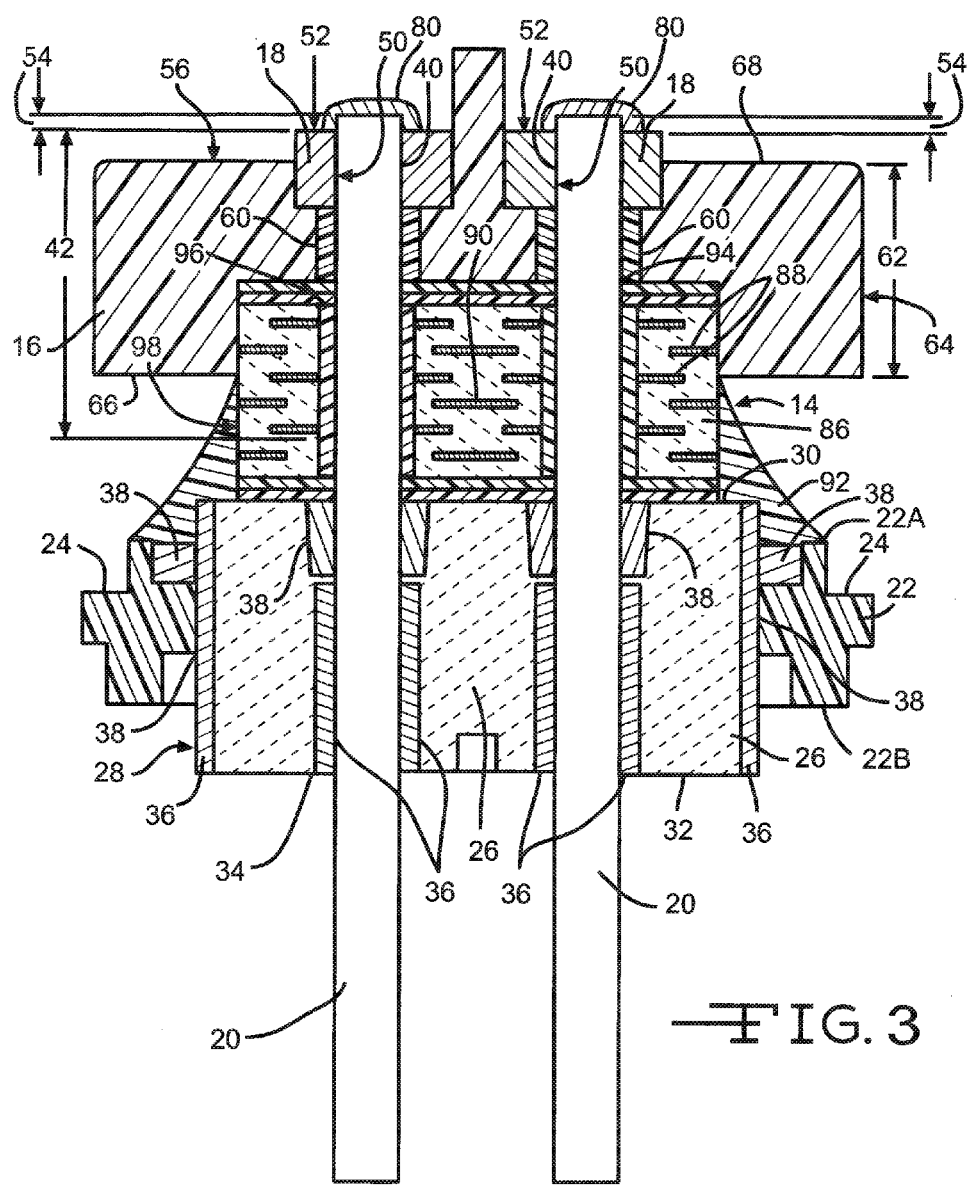
FIG. 3 is cross sectional view of the filter capacitor assembly shown in FIG. 1.

Referring now to the drawings, FIGS. 1 and 3 show an internally grounded feedthrough capacitor assembly 10 comprising a feedthrough 12 supporting a discoidal filter capacitor 14, a protective cap 16, and a plurality of terminal blocks 18.

The feedthrough filter assembly 10 is useful with medical devices, preferably implantable devices such as pacemakers, cardiac defibrillators, cardioverter defibrillators, cochlear implants, neurostimulators, internal drug pumps, deep brain stimulators, hearing assist devices, incontinence devices, obesity treatment devices, Parkinson's disease therapy devices, bone growth stimulators, and the like. The feedthrough 12 portion of the assembly 10 includes terminal pins 20 that provide for coupling, transmitting and receiving electrical signals to and from a patient's heart, while hermetically sealing the interior of the medical instrument against ingress of patient body fluids that could otherwise disrupt instrument operation or cause instrument malfunction. While not necessary for accomplishing these functions, it is desirable to attach the filter capacitor 14 to the feedthrough 12 for suppressing or decoupling undesirable EMI signals and noise transmission into the interior of the medical device.

More particularly, the feedthrough 12 of the feedthrough filter capacitor assembly 10 comprises a ferrule 22 defining an insulator-receiving bore formed by a ferrule sidewall extending from a first ferrule end 22A to a second ferrule end 22B, the ferrule sidewall surrounding an insulator 26. Suitable electrically conductive materials for the ferrule 22 include titanium, tantalum, niobium, stainless steel or combinations of alloys thereof, the former being preferred. The ferrule 22 may be of any geometry, non-limiting examples being round, rectangle, and oblong. A surrounding flange 24 (FIG. 3) extends from the ferrule 22 to facilitate attachment of the feedthrough 12 to the casing (not shown) of, for example, one of the previously described implantable medical devices. The method of attachment may be by laser welding or other suitable methods.

The insulator 26 is of a ceramic material such as of alumina, zirconia, zirconia toughened alumina, aluminum nitride, boron nitride, silicon carbide, glass or combinations thereof. Preferably, the insulating material is alumina, which is highly purified aluminum oxide, and comprises a sidewall 28 extending to a first upper side or end 30 and a second lower side or end 32. The insulator 26 is also provided with bores 34 that receive the terminal pins 20 passing therethrough. A layer of metal 36, referred to as metallization, is applied to the insulator sidewall 28 and to the sidewall of the terminal pin bores 34 to aid a braze material 38 in hermetically sealing between the ferrule 22 and the outer sidewall 28 of the insulator 26 and between the terminal pins 20 and the bores 34 of the insulator 26, respectively.

Suitable metallization materials 36 include titanium, titanium nitride, titanium carbide, iridium, iridium oxide, niobium, tantalum, tantalum oxide, ruthenium, ruthenium oxide, zirconium, gold, palladium, molybdenum, silver, platinum, copper, carbon, carbon nitride, and combinations thereof. The metallization layer may be applied by various means including, but not limited to, sputtering, electron-beam deposition, pulsed laser deposition, plating, electroless plating, chemical vapor deposition, vacuum evaporation, thick film application methods, and aerosol spray deposition, and thin cladding. Parylene, alumina, silicone, fluoropolymers, and mixtures thereof are also useful metallization materials.

Non-limiting examples of braze materials 38 include gold, gold alloys, and silver. Then, if the feedthrough 14 is used where it will contact bodily fluids, the resulting brazes do not need to be covered with a biocompatible coating material. In other embodiments, if the brazes are not biocompatible, for example, if they contain copper, they are coated with a layer/coating of biocompatible/biostable material. Broadly, the biocompatibility requirement is met if contact of the braze/coating with body tissue and blood results in little or no immune response from the body, especially thrombogenicity (clotting) and encapsulation of the electrode with fibrotic tissue. The biostability requirement means that the braze/coating remains physically, electrically, and chemically constant and unchanged over the life of the patient.

According to one embodiment of the invention, the terminal pins 20 are preferably composed of a first metal comprising a refractory metal. A refractory metal is herein defined as a metal that is resistant to heating and has a melting temperature above about 1,800° C. Non-limiting examples of refractory metals include niobium, molybdenum, tantalum, tungsten, rhenium, titanium, vanadium, zirconium, hafnium, osmium, iridium, and alloys thereof. In a more preferred embodiment, the terminal pins 20 comprise niobium and niobium alloys.

As shown in FIGS. 1-5, each terminal pin 20 is received in a throughbore 40 of the terminal block 18. In a preferred embodiment, a proximal end portion 42 of the terminal pin 20 is received in the throughbore 40 of the terminal block 18. Terminal blocks 18 have a terminal block length 44, a terminal block width 46 and a terminal block height 48 (FIG. 4). In a preferred embodiment, the length 44 of the terminal block 18 ranges from about 1 mm to about 5 mm, the width 46 of the terminal block 18 ranges from about 1 mm to about 5 mm and the thickness 48 of the terminal block 18 ranges from about 0.05 mm to about 5 mm.

It is preferred that the terminal block 18 is composed of a second metal comprising an electrically conductive metal. Non-limiting examples of conductor block 18 second metals include nickel, titanium, gold, silver, platinum, palladium, stainless steel, MP35N (ASTM Material Designation: 35Co-35Ni-20Cr-10Mo), and alloys thereof. In a more preferred embodiment, terminal blocks 18 are composed of nickel or a nickel alloy.

Each throughbore 40 of the terminal block 18 is preferably constructed with a diameter ranging from about 0.01 mm to about 0.10 mm such that the terminal pin 20 can pass therethrough. It is preferred that the terminal pin 20 is positioned such that the bore wall 50 of the terminal block 18 circumferentially surrounds the diameter of the terminal pin 20. It is further preferred that the proximal end portion 42 of the terminal pin 20 may reside above or below the topside surface 52 of the terminal block 18. In a preferred embodiment, the terminal pin 20 may reside from about 0.02 mm to about 0.2 mm above or below the top surface 52 of the terminal block 18. This preferred alignment of the end 54 of the terminal pin 20 to the terminal block 18 reduces mechanical stresses in the joining of the first metal comprising the pin 20 to the second metal comprising the block 18, thereby increasing the robustness of the joint.

Furthermore, each terminal block 18 is preferably positioned on the topside 56 of the protective cap 16. In a preferred embodiment, the terminal block 18 resides within a slot 58 formed into the topside surface 56 of the protective cap 16 (FIGS. 1, 4). Each slot 58 is dimensioned such that the width 46 and length 44 of the terminal block 18 fit within the slot 58.

In addition, the terminal pins 20 are preferably positioned such that they are received through a throughbore 60 of the protective cap 16. More specifically, the proximal portion 42 of the terminal pin 20 is received through the respective throughbores 60 and 40 of the protective cap 16 and the terminal block 18. The protective cap 16 is positioned in a more distal location of the terminal pin 20 than the terminal block 18 (FIG. 3).

In a preferred embodiment, the protective cap 16 is composed of a biocompatible polymeric material that can withstand temperatures up to about 300° C. It is preferred that the protective cap 16 is composed of a polyoxymethylene copolymer such as CELCON® M450 or HOSTAFORM® C 52021 manufactured by Ticona of Florence, Ky. Other non-limiting materials comprising the protective cap 16 include silicone rubber, acrylonitrile butadiene styrene (ABS) and polyether ether ketone (PEEK).

In a preferred embodiment, as shown in FIGS. 1, 3, and 4, the protective cap 16 has a height 62 defined by a protective cap sidewall 64 extending from a first protective cap end 66 to a second protective cap end 68, wherein the terminal pin 20 extends through a protective cap throughbore 60 extending from the first protective cap end 66 to the second protective cap end 68. As shown in FIG. 3, the terminal block 18 is positioned in a stacked relationship on the topside surface 56 of the protective cap 16. The respective throughbores 60, 40 of the protective cap 16 and terminal block 18 are aligned such that the proximal region 42 of the terminal pin 20 resides therethrough. It should be noted however, that the protective cap 16 may or may not be incorporated with a feedthrough assembly 10 comprising a capacitor 14.

In addition, the protective cap 16 is constructed such that a plurality of walls 70 project from the topside surface 56 of the protective cap 16. More preferably, these walls 70 interconnect at a central junction 72 (FIG. 4). These walls 70 have a preferred wall thickness 74 of about 0.5 mm to about 5 mm, a preferred wall height 76 of about 1 mm to about 10 mm, and a preferred wall length 78 of about 1 mm to about 10 mm. The walls 70 electrically insulate the terminal blocks 18 from each other.

In a preferred embodiment, a partial weld 80 is formed between the first metal of the terminal pin 20 and the second metal of the terminal block 18. More specifically, a portion of the proximal end region 42 of the terminal pin 20 is joined to a portion of the throughbore 40 diameter of the terminal block 18 surrounding the terminal pin 18. As shown in FIGS. 1-5, this partial weld 80 is formed of a shape similar to that of a partial "button". As illustrated in FIG. 3, this partial "button" shaped weld 80 fills a portion of the gap 82 between the terminal block 18 and terminal pin 20. Alternatively, this partial "button" shaped weld 80 may be formed above the top surface 52 of the terminal block 18. In this embodiment, the terminal pins 20 protrude above the top surface 52 of the terminal block 18.

In a preferred embodiment, an alloy is formed comprising a mixture of the first metal of the terminal pin 20 and the second metal of the terminal block 18. This partial weld 80 enables the joining of these two dissimilar metals, the first metal and second metal, of the terminal pin 20 and terminal block 18, respectively, such that the adjacent protective cap 16 is not deformed or damaged.

In a preferred embodiment, heat generated during the welding process is localized to a portion of the terminal pin 20 and terminal block 18. A sufficient amount of heat is generated to effectively form the alloy joining the two dissimilar first and second metals without generating too much heat such that the protective cap 16 and other adjacent materials of the feedthrough assembly 10 are damaged.

In a preferred embodiment, a laser welding instrument such as a Lasag® model SLS200 is used to partially join the terminal pin 20 to the terminal block 18. In a preferred embodiment, a laser pulse frequency of between about 2 Hz to about 10 Hz is used with a pulse width of between about 0.5 ms to about 2.0 ms generating a welding energy from about 0.5 J to about 2.0 J is used to weld the dissimilar metals together. These preferred laser welding parameters provide a weld 80 that sufficiently joins the two dissimilar metals of the terminal pin 20 and the terminal block 18 such that the adjacent protective cap 16 is not damaged or deformed.

Figure 2:
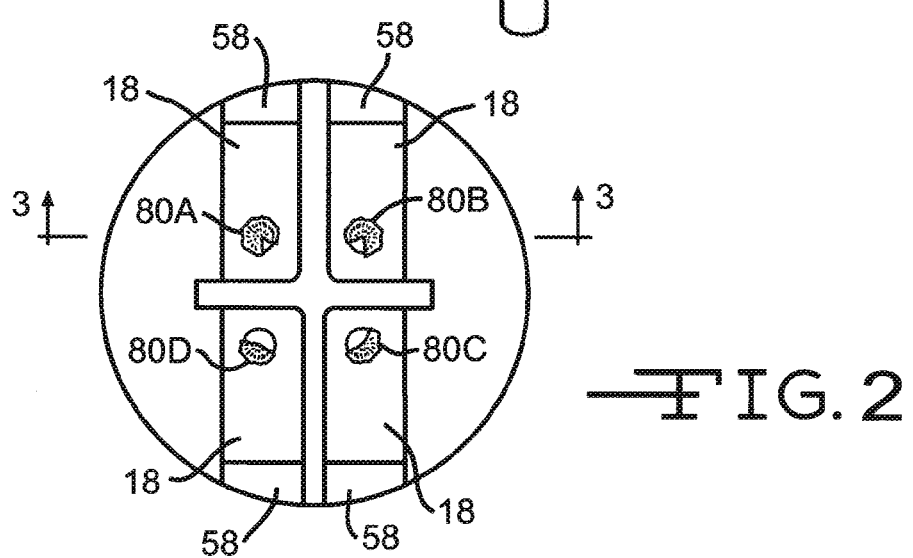
FIG. 2 is top view of the feedthrough filter capacitor assembly shown in FIG. 1.

In a preferred embodiment, illustrated in FIGS. 1, 2 and 4, a partial weld 80 covering about 10 percent to about 80 percent of the perimeter 83 (FIG. 5) of the terminal pin 20 is joined to the terminal block 18. In a more preferred embodiment, about 20 percent to about 60 percent of the perimeter 83 of the terminal pin 20 is welded to the terminal block 18. FIG. 2 further illustrates these featured embodiments of the partial weld 80. A partial weld of about 80 percent is identified as 80A, a 60 percent partial weld embodiment is identified as 80B, a 40 percent partial weld embodiment is identified as 80C, and a 20 percent partial weld is identified as 80D.

These partial weld parameters provide a weld of sufficient strength and robustness that allows for the joining of the refractory metal, the first metal, of the terminal pin 20 to that of the terminal block 18. In addition, these metals are joined without generating enough heat to deform the adjacent polymeric protective cap 16. Furthermore, these preferred partial welding embodiments minimize the amount of heat transferred into the terminal block 18. Minimizing heat transfer into the terminal block 18 minimizes heat radiated out of the terminal block 18, to thereby help prevent degradation of the protective cap 16. Therefore, the preferred partial weld process of the present invention minimizes heat absorption and heat radiation from the terminal block 18. On the other hand, excessive radiated heat may contribute to thermal degradation of the adjacent materials of the feedthrough assembly 10.

In a preferred embodiment, the unwelded portion of the partial weld 80 faces the central junction as shown in FIGS. 1, 2 4 and 5. This further helps prevent damage to the protective cap 16 as there is very little, if any, heat radiated into a corner 85 formed where two walls 70 of the cap 16 meet at the junction 72.

As further shown in FIGS. 2, 4 and 5, the feedthrough assembly 10 includes the filter capacitor 14 that provides for filtering undesirable EMI signals before they can enter the device housing via the terminal pins 20. The filter capacitor 14 comprises a ceramic or ceramic-based dielectric monolith 86 having multiple capacitor-forming conductive electrode plates formed therein. The capacitor dielectric 86 preferably has a circular cross-section matching the cross-section of the ferrule 22 and supports a plurality of spaced-apart layers of first or "active" electrode plates 88 in spaced relationship with a plurality of spaced apart layers of second or "ground" electrode plates 90. The filter capacitor 14 is preferably joined to the feedthrough 12 adjacent to the insulator side 30 by an annular bead 92 of conductive material, such as a solder or braze ring, or a thermal-setting conductive adhesive, and the like. The dielectric 86 includes lead bores 94 provided with an inner surface metallization layer. The terminal pins 20 pass there through and are conductively coupled to the active plates 88 by a conductive braze material 96 contacting between the terminal pins 20 and the bore metallization. In a similar manner, the ground plates 90 are electrically connected through an outer surface metallization 98 and the conductive material 92 to the ferrule 22.

It is appreciated that various modifications to the invention concepts described herein may be apparent to those of ordinary skill in the art without departing from the scope of the present invention as defined by the appended claims.

What is claimed is:

1. A feedthrough assembly, which comprises:
   a) an insulator of electrically non-conductive material comprising an insulator sidewall, having an outer insulator surface extending from a first insulator end to a second insulator end, wherein the insulator has at least one terminal pin bore extending there through to the first and second insulator ends;
   b) a terminal pin comprising a first metal received in the terminal pin bore, the terminal pin having a terminal pin sidewall extending from a first terminal pin portion having a first terminal pin end to a second terminal pin end, wherein the opposed first and second terminal pin ends are spaced from the respective first and second insulator ends, and wherein the first terminal pin portion has a terminal pin perimeter;
   c) a ferrule of an electrically conductive material comprising a ferrule opening defined by a surrounding ferrule sidewall having an inner ferrule surface, wherein the insulator is supported in the ferrule opening;
   d) a terminal block of a second metal and comprising a terminal block sidewall, extending to opposed first and second terminal block ends, the terminal block having at least one terminal block bore extending there through to the first and second terminal block ends, wherein the first terminal pin portion extends through the terminal block bore with the first terminal pin end spaced above the first end of the terminal block, and wherein the second end of the terminal block faces the insulator;
   e) a first braze material extending from a first metallization contacting the terminal pin bore to the first metal of the terminal pin, thereby hermetically sealing the terminal pin to the insulator;
   f) a second braze material extending from a second metallization contacting the outer insulator surface to the inner ferrule surface to thereby hermetically seal the insulator to the ferrule; and
   g) a weld connecting from about 10 percent to about 60 percent of the terminal pin perimeter at the first terminal pin portion to the first terminal block end.

2. The feedthrough assembly of claim 1 wherein the first metal of the terminal pin comprises a refractory metal.

3. The feedthrough assembly of claim 1 wherein the first metal of the terminal pin is selected from the group consisting of niobium, molybdenum, tantalum, tungsten, rhenium, titanium, vanadium, zirconium, hafnium, osmium, iridium, and alloys thereof.

4. The feedthrough assembly of claim 1 wherein the weld is a laser weld.

5. The feedthrough assembly of claim 4 wherein the laser weld is characterized as having been formed by a laser at a welding energy of from about 0.5 joule to about 2.0 joule (J).

6. The feedthrough assembly of claim 4 wherein the laser weld is characterized as having been formed by a laser at a welding pulse frequency of from about 2 hertz (Hz) to about 10 hertz (Hz).

7. The feedthrough assembly of claim 4 wherein the laser weld is characterized as having been formed by a laser at a welding pulse width of from about 0.5 milliseconds (msec) to about 2.0 milliseconds (msec).

8. The feedthrough assembly of claim 1 wherein the weld connects from about 20 percent to about 80 percent of the perimeter of the terminal pin to the terminal block.

9. The feedthrough assembly of claim 1 further comprising a protective cap comprising a protective cap sidewall extending from a first protective cap end to a second protective cap end, wherein the protective cap is positioned between the second end of the terminal block and the first end of the insulator with the terminal pin residing in a protective cap throughbore extending to the first and second protective cap ends.

10. The feedthrough assembly of claim 9 wherein the protective cap is composed of a biocompatible polymeric material.

11. The feedthrough assembly of claim 9 wherein the terminal block is positioned in a slot at the first protective cap end.

12. The feedthrough assembly of claim 1 wherein the insulator and the terminal block have at least two respective terminal pin bores and terminal block bores with at least two terminal pins residing therein, and wherein welds connect from about 10 percent to about 60 percent of the first portion of each of the terminal pins to the first end of the terminal block with a remaining unwelded portion of the respective perimeters of the first terminal pin portions facing each other.

13. The feedthrough assembly of claim 1 wherein the second metal of the terminal block is selected from the group consisting of nickel, titanium, gold, silver, platinum, palladium, stainless steel, MP35N (35Co-35Ni-20Cr-10Mo), and alloys thereof.

14. The feedthrough assembly of claim 1 wherein the first terminal pin end is either spaced above or recessed below the first terminal block end.

15. A method for providing a feedthrough assembly, comprising the steps of:
   a) as providing a feedthrough comprising:
      i) an insulator of electrically non-conductive material comprising an insulator sidewall having an outer insulator surface extending from a first insulator end to a second insulator end, wherein the insulator has at least one terminal pin bore extending there through to the first and second insulator ends;
      ii) a terminal pin comprising a first metal received in the terminal pin bore, the terminal pin having a terminal pin sidewall extending from a first terminal pin portion having a first terminal pin end to a second terminal pin end, wherein the opposed first and second terminal pin ends are spaced from the respective first and second insulator ends, and wherein the first terminal pin portion has a terminal pin perimeter;
      iii) a ferrule of an electrically conductive material comprising a ferrule opening defined by a surrounding ferrule sidewall having an inner ferrule surface, wherein the insulator is supported in the ferrule opening;
      iv) a terminal block of a second metal and comprising a terminal block sidewall extending to opposed first and second terminal block ends, the terminal block having at least one terminal block bore extending there through to the first and second terminal block ends, wherein the first terminal pin portion extends through the terminal block bore with the first terminal pin end spaced above the first end of the terminal block and the second end of the terminal block facing the insulator;

v) a first braze material extending from a first metallization contacting the terminal pin bore to the first metal of the terminal pin, thereby hermetically sealing the terminal pin to the insulator; and vi) a second braze material extending from a second metallization contacting the outer insulator surface to the inner ferrule surface to thereby hermetically seal the insulator to the ferrule; and b) welding from about 10 percent to about 60 percent of the terminal pin perimeter at the first terminal pin portion to the first terminal block end.

16. The method of claim 15 including providing the first metal of the terminal pin comprising a refractory metal.

17. The method of claim 15 including selecting the terminal pin from the group consisting of niobium, molybdenum, tantalum, tungsten, rhenium, titanium, vanadium, zirconium, hafnium, osmium, iridium, and alloys thereof.

18. The method of claim 15 including providing the weld as a laser weld.

19. The method of claim 18 including welding the first portion of the terminal pin to the first end of the terminal block by applying a laser weld energy of from about 0.5 joule (J) to about 2.0 joule (5), a welding pulse frequency of from about 2 hertz (Hz) to about 10 hertz (Hz), and a welding pulse width of from about 0.5 milliseconds (msec) to about 2.0 milliseconds (msec) to at least one of the terminal pin and the terminal block.

20. The method of claim 15 including joining from about 20 percent to about 80 percent of the perimeter of the terminal pin to the terminal block.

21. The method of claim 15 including providing a protective cap comprising a protective cap sidewall extending from a first protective cap end to a second protective cap end, wherein the protective cap is positioned between the second end of the terminal block and the first end of the insulator with the terminal pin residing in a protective cap throughbore extending to the first and second protective cap ends.

22. The method of claim 21 including providing the protective cap composed of a biocompatible polymeric material.

23. The method of claim 21 including providing the terminal block in a slot formed at the first protective cap end.

24. The method of claim 15 including providing the insulator and the terminal block having at least two respective terminal pin bores and terminal block bores with at least two terminal pins residing therein and further welding from about 10 percent to about 60 percent of the first portion of each of the terminal pins to the first end of the terminal block with a remaining unwelded portion of the respective perimeters of the first portions of the terminal pins facing each other.

25. The method of claim 15 including selecting the second metal of the terminal block from the group consisting of nickel, titanium, gold, silver, platinum, palladium, stainless steel, MP35N (35Co-35Ni-20Cr-10Mo), and alloys thereof.

26. A feedthrough assembly, which comprises:

a) an insulator of electrically non-conductive material comprising an insulator sidewall having an outer insulator surface extending from a first insulator end to a second insulator end, wherein the insulator has at least one terminal pin bore extending there through to the first and second insulator ends;

b) a terminal pin comprising a first metal received in the terminal pin bore, the terminal pin having a terminal pin sidewall extending from a first terminal pin portion having a first terminal pin end to a second terminal pin end, wherein the opposed first and second terminal pin ends are spaced from the respective first and second insulator ends, and wherein the first terminal pin portion has a terminal pin perimeter;

c) a ferrule of an electrically conductive material comprising a ferrule opening defined by a surrounding ferrule sidewall having an inner ferrule surface, wherein the insulator is supported in the ferrule opening;

d) a terminal block of a second metal and comprising a terminal block sidewall extending to opposed first and second terminal block ends, the terminal block having at least one terminal block bore extending there through to the first and second terminal block ends, wherein the first terminal pin portion resides in the terminal block bore with the first terminal pin end recessed below the first terminal block end, and wherein the second end of the terminal block faces the insulator;

e) a first braze material extending from a first metallization contacting the terminal pin bore to the first metal of the terminal pin, thereby hermetically sealing the terminal pin to the insulator;

f) a second braze material, extending from a second metallization contacting the outer insulator surface to the inner ferrule surface to thereby hermetically seal the insulator to the ferrule; and g) a weld connecting from about 10 percent to about 60 percent of the terminal pin perimeter at the first terminal pin end to the first terminal block end.

\* \* \* \* \*

UNITED STATES PATENT AND TRADEMARK OFFICE
CERTIFICATE OF CORRECTION

PATENT NO. : 8,648,255 B2  
APPLICATION NO. : 13/112041  
DATED : February 11, 2014  
INVENTOR(S) : Ken Talamine et al.

Page 1 of 1

It is certified that error appears in the above-identified patent and that said Letters Patent is hereby corrected as shown below:

In the Claims

Column 7, line 15 (Claim 1, line 3) after the word "sidewall" delete the ","

Column 7, line 33 (Claim 1, line 21) after the word "sidewall" delete the ","

Column 8, line 26 (Claim 12, line 4) after the word "therein" delete the ","

Column 8, line 41 (Claim 15, line 3) after "a)" delete the word "as"

Column 9, line 26 (Claim 19, line 4) delete "(5)" and insert --(J)--

Column 10, line 41 (Claim 26, line 3) after the word "material" delete the ","

Signed and Sealed this  
Fourteenth Day of October, 2014

Michelle K. Lee  
*Deputy Director of the United States Patent and Trademark Office*